(12) United States Patent
Blackler et al.

(10) Patent No.: US 6,806,280 B1
(45) Date of Patent: Oct. 19, 2004

(54) POLYMORPH OF 5-[4-[2-(N-METHYL-N(2-PYRIDYL)AMINO)ETHOXY]BENZYL]-THIAZOLIDINE-2,4-DIONE, MALEIC ACID SALT

(75) Inventors: Paul David James Blackler, Cadiz (ES); Christine Marie Browne, Carrigaline (IE); Timothy G. Coakley, Carrigaline (IE); Robert Gordon Giles, Tonbridge (GB); Gillian Morrissey, Carrigaline (IE)

(73) Assignees: SmithKline Beecham p.l.c., Brentford (GB); SmithKline Beecham (Cork) Limited, Carrigaline (IE)

( * ) Notice: Subject to any disclaimer, the term of this patent is extended or adjusted under 35 U.S.C. 154(b) by 0 days.

(21) Appl. No.: 10/048,123
(22) PCT Filed: Apr. 19, 2000
(86) PCT No.: PCT/GB00/01520
§ 371 (c)(1),
(2), (4) Date: Dec. 3, 2001
(87) PCT Pub. No.: WO00/64896
PCT Pub. Date: Nov. 2, 2000

(30) Foreign Application Priority Data

Apr. 23, 1999 (GB) .............................................. 9909473
May 25, 1999 (GB) .............................................. 9912196

(51) Int. Cl.[7] ........................ A61K 31/44; C07D 417/00
(52) U.S. Cl. .................................... 514/342; 546/269.7
(58) Field of Search ........................ 546/269.7; 514/342

(56) References Cited

U.S. PATENT DOCUMENTS

| | | | |
|---|---|---|---|
| 5,002,953 A | 3/1991 | Hindley | 514/275 |
| 5,741,803 A | 4/1998 | Pool et al. | 514/342 |
| 5,910,592 A | 6/1999 | Pool et al. | 546/269.7 |
| 2002/0099081 A1 | 7/2002 | Sasse et al. | 514/340 |
| 2003/0120078 A1 | 6/2003 | Sasse et al. | 546/269.7 |

FOREIGN PATENT DOCUMENTS

| | | | |
|---|---|---|---|
| CN | 1277965 | 12/2000 | |
| EP | 0 306 228 B1 | 11/1999 | |
| WO | WO 93/10254 | 3/1993 | |
| WO | WO 94/05659 | 3/1994 | |
| WO | WO 95/21603 | 8/1995 | |
| WO | 9837073 | * 8/1998 | |
| WO | WO 98-55122 | * 10/1998 | |
| WO | WO 98/55122 | 12/1998 | A61K/31/44 |
| WO | WO 99/31093 | 6/1999 | |
| WO | WO 00/64892 | 11/2000 | |
| WO | WO 00/64893 | 11/2000 | |
| WO | WO 02/26737 | 4/2002 | |

OTHER PUBLICATIONS

Cantello, et al., "The Synthesis of BRL 49653 —A Novel and Potent Antihyperglycaemic Agent". *Bioorganic& Medicinal Chemistry Letters*, 4(*10*): 1181–1184 (1994).
The American Heritage Dictionary of the English Language: Fourth Edition. 2000. http://www.bartleby.com/61/32/I0253200.html.

(List continued on next page.)

*Primary Examiner*—Johann Richter
*Assistant Examiner*—Binta Robinson
(74) *Attorney, Agent, or Firm*—Kathryn I. Sieburth; Mary E. McCarthy; Charles M. Kinzig (57) ABSTRACT

A polymorphic form of 5-[4-[2-(N-methyl-N-(2-pyridyl)amino)ethoxy]benzyl]-thiazolidine-2, 4-dione, maleic acid salt (the "Polymorph") characterized in that it provides: (i) an infra red spectrum containing peaks at 1763, 912, 856 and 709 cm$^{-1}$; and/or (ii) a Raman spectrum containing peaks at 1762, 1284, 912 and 888 cm$^{-1}$; and/or (iii) a solid-state $^{13}$C nuclear magnetic resonance spectrum containing peaks at 111.0, 113.6, 119.8, 129.1, 130.9, 131.8, 134.7, 146.5, 152.7, 157.5, 169.5, 171.0, 178.7 ppm; and/or (v) an X-ray powder diffraction (XRPD) pattern which gives calculated lattice spacings at 5.87, 5.30, 4.69, 4.09, 3.88, 3.61, 3.53 and 3.46 Angstroms; a process for preparing such a compound, a pharmaceutical composition containing such a compound and the use of such a compound in medicine.

19 Claims, 4 Drawing Sheets

Infrared Spectrum of the Polymorph

OTHER PUBLICATIONS

Haleblian, et al., "Pharmaceutical Applications of Polymorphism", *Journal of Pharmaceutical Sciences,* 58(*8*): 911–929 (1969).

J. Halebian and W. McCrone, "Pharmaceutical Applications of Polymorphism", *Journal of Pharmaceutical Sciences*, vol. 58, No. 8, pp. 911–929 (1969).

* cited by examiner

Figure 1:
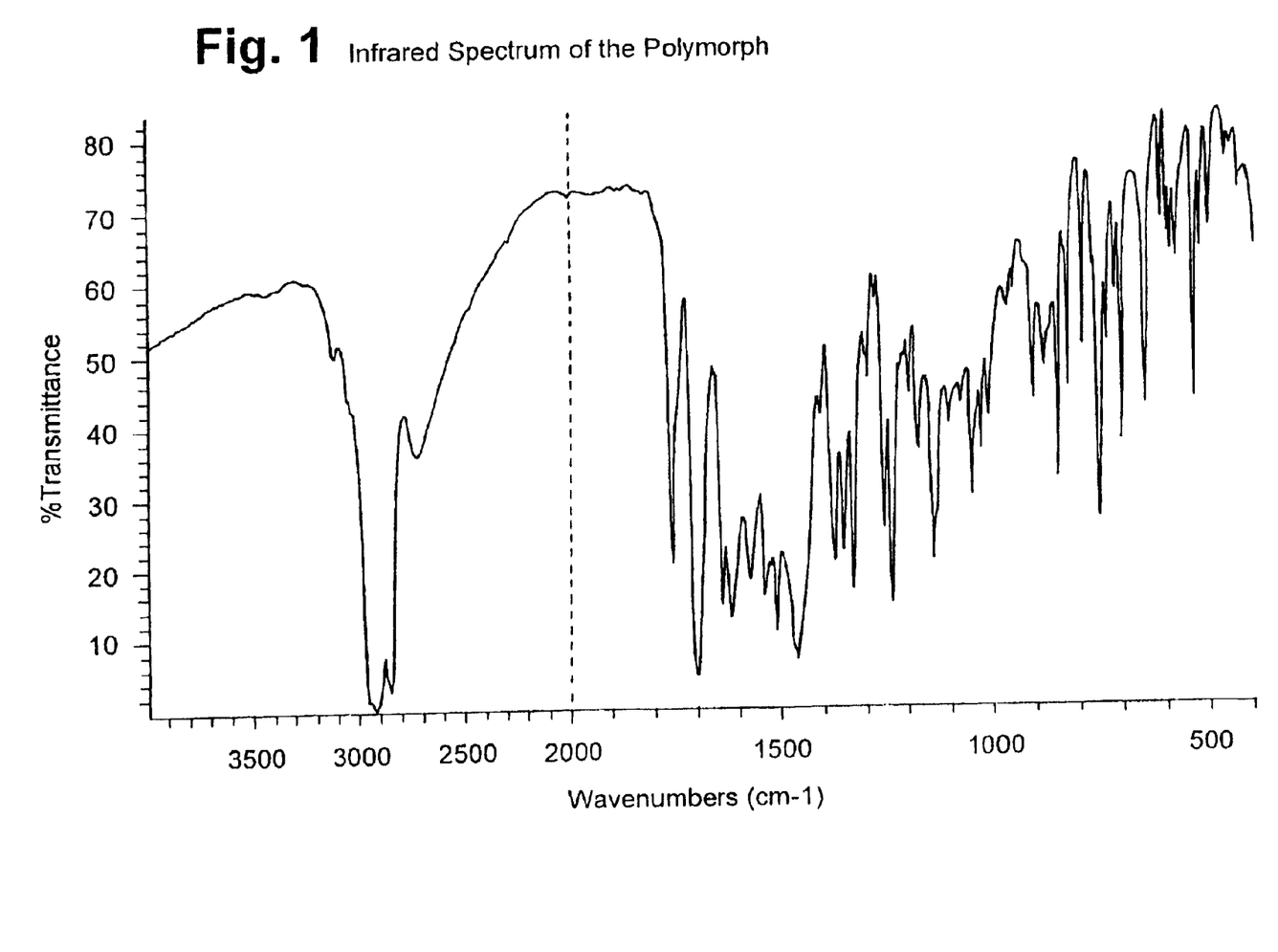

Fig. 1 Infrared Spectrum of the Polymorph

Figure 2:
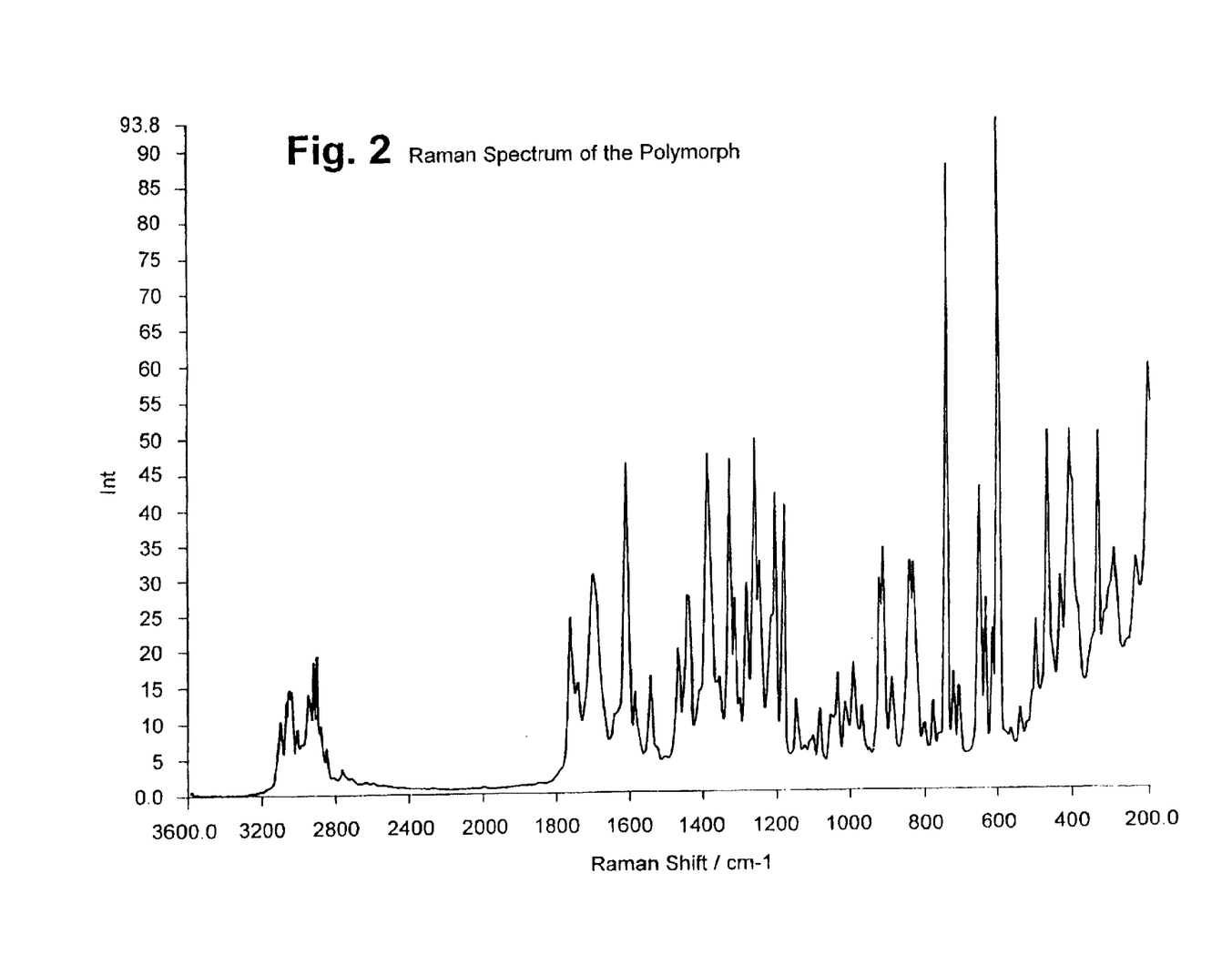
Figure 3:
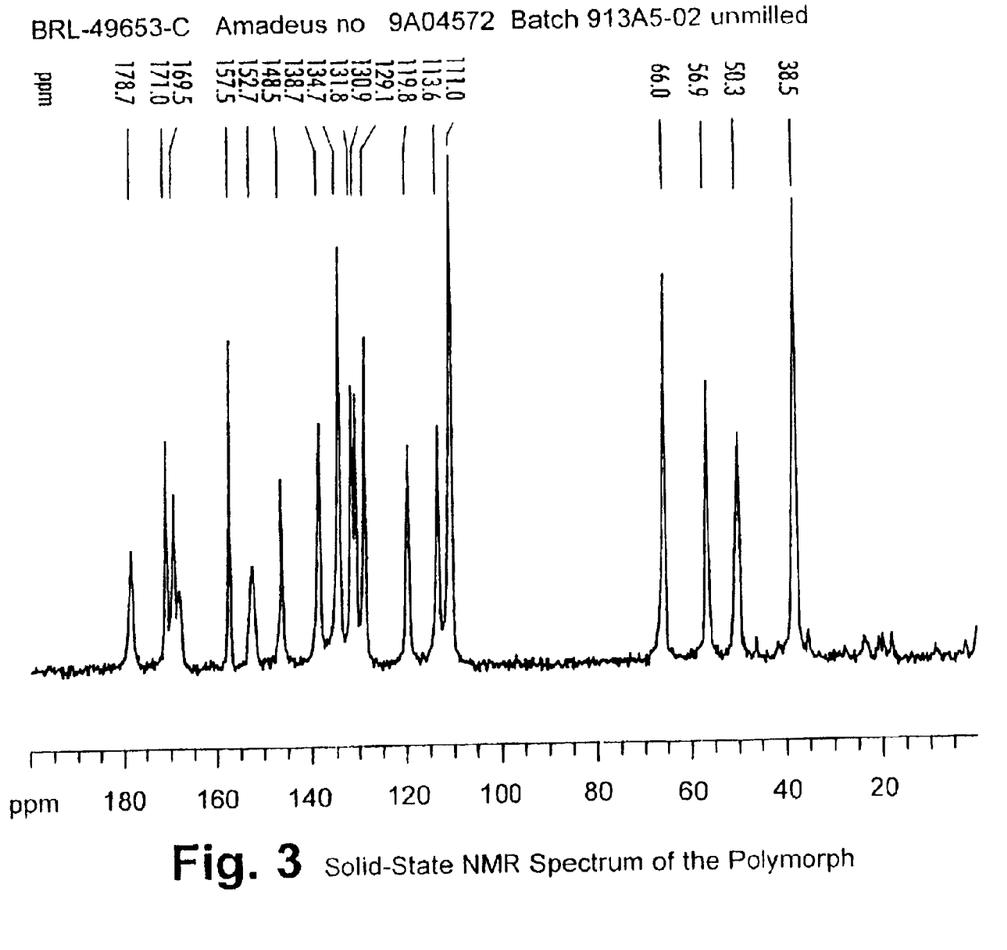

Fig. 2 Raman Spectrum of the Polymorph

Figure 4:
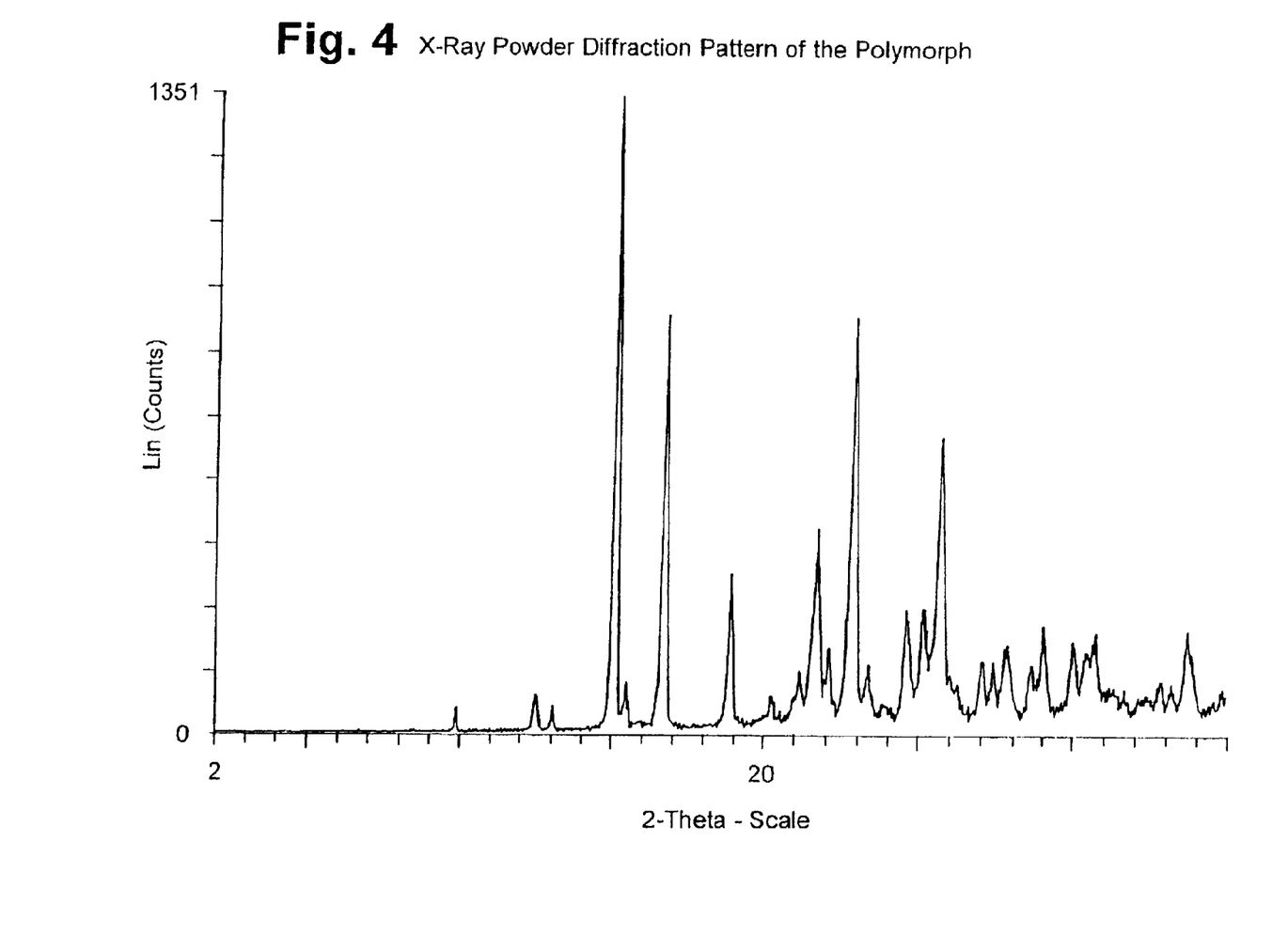

Fig. 4 X-Ray Powder Diffraction Pattern of the Polymorph

POLYMORPH OF 5-[4-[2-(N-METHYL-N(2-PYRIDYL)AMINO)ETHOXY]BENZYL]-THIAZOLIDINE-2,4-DIONE, MALEIC ACID SALT

This application is a 371 of PCT/GB00/01520 filed Apr. 19, 2000.

This invention relates to a novel pharmaceutical, to a process for the preparation of the pharmaceutical and to the use of the pharmaceutical in medicine.

International Patent Application, Publication Number WO94/05659 discloses certain thiazolidinedione derivatives having hypoglycaemic and hypolipidaemic activity including 5-[4-[2-(N-methyl-N-(2-pyridyl)amino)ethoxy]benzyl]thiazolidine-2,4-dione, maleic acid salt (hereinafter also referred to as "Compound (I)").

International Patent Applications, Publication Numbers WO99/31093, WO99/31094 and WO99/31095 each disclose distinct hydrates of Compound (I).

It has now been discovered that Compound (I) exists in a novel polymorphic form which is particularly suitable for bulk preparation and handling. The novel form can be prepared by an efficient, economic and reproducible process particularly suited to large-scale preparation.

The novel polymorphic form ('the Polymorph') also has useful pharmaceutical properties and in particular it is indicated to be useful for the treatment and/or prophylaxis of diabetes mellitus, conditions associated with diabetes mellitus and certain complications thereof.

Accordingly, the present invention provides a polymorphic form of 5-[4-[2-(N-methyl-N-(2-pyridyl)amino)ethoxy]benzyl]thiazolidine-2,4-dione, maleic acid salt characterised in that it:

(i) provides an infra red spectrum containing peaks at 1763, 912, 856 and 709 $cm^{-1}$; and/or (ii) provides a Raman spectrum containing peaks at 1762, 1284, 912 and 888 $cm^{-1}$; and/or (iii) provides a solid-state $^{13}C$ nuclear magnetic resonance spectrum containing peaks at 111.0, 113.6, 119.8, 129.1, 130.9, 131.8, 134.7, 138.7, 146.5, 152.7, 157.5, 169.5, 171.0, 178.7 ppm; and/or (iv) provides an X-ray powder diffraction (XRPD) pattern which gives calculated lattice spacings at 5.87, 5.30, 4.69, 4.09, 3.88, 3.61, 3.53 and 3.46 Angstroms.

In one favoured aspect, the Polymorph provides an infra-red spectrum substantially in accordance with FIG. I.

In one favoured aspect, the Polymorph provides a Raman spectrum substantially in accordance with FIG. II.

In one favoured aspect, the Polymorph provides a solid-state nuclear magnetic resonance spectrum substantially in accordance with FIG. III and/or Table I.

In one favoured aspect, the Polymorph provides an X-ray powder diffraction (XRPD) pattern substantially in accordance with FIG. IV and/or Table II.

The present invention encompasses the Polymorph isolated in pure form or when admixed with other materials, for example the known forms of Compound I (or the "Original Polymorph") or any other material.

Thus in one aspect there is provided the Polymorph in isolated form.

In a further aspect there is provided the Polymorph in pure form.

In yet a further aspect there is provided the Polymorph in crystalline form.

The invention also provides a process for preparing the Polymorph, characterised in that Compound (I) is suspended in acetone, preferably under an inert atmosphere such as nitrogen, and stirred at an elevated temperature, preferably reflux temperature, for an extended period of time, for example 17 hours, after which time the Polymorph is isolated from the reaction mixture.

In an alternative process a solution of Compound (I) in denatured ethanol at an elevated temperature, for example 50° C., is seeded with crystals of the Polymorph then cooled, preferably to a temperature in the range of from 20–25° C., so as to provide the Polymorph, after which time the Polymorph is recovered from the denatured ethanol. The solution of Compound (I) in the denatured ethanol is conveniently prepared by dissolving Compound (I) in the required amount of denatured ethanol at an elevated temperature, for example 60° C.

Typically the Polymorph is recovered from the reaction by filtration and subsequent drying, usually at an elevated temperature, for example 50° C.

In a further aspect, the invention provides a process for converting Polymorph to Compound (I), wherein a solution of Polymorph in a suitable solvent, such as acetone or ethanol, is seeded with Compound (I). Generally, the solution of Polymorph is obtained by dissolving Polymorph at an elevated temperature in the solvent, such as acetone or ethanol.

Compound (I) is prepared according to known procedures, such as those disclosed in WO94/05659. The disclosures of WO94/05659 are incorporated herein by reference.

For the avoidance of doubt the term "Compound (I)" as used herein refers to the form of 5-[4-[2-(N-methyl-N(2-pyridyl)amino)ethoxy]benzyl]thiazolidine-2,4-dione, maleic acid salt as disclosed an characterised in International Patent Application, Publication Number WO94/05659.

When used herein "denatured ethanol" means ethanol containing small amounts of methanol, usually up to 5% v/v of methanol, such as from 0.9% v/v to 5% v/v of methanol, for example ethanol containing 4% v/v of methanol.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As mentioned above the compound of the invention has useful therapeutic properties: The present invention accordingly the Polymorph for use as an active therapeutic substance.

More particularly, the present invention provides the Polymorph for use in the treatment and/or prophylaxis of diabetes mellitus, conditions associated with diabetes mellitus and certain complications thereof.

The Polymorph may be administered per se or, preferably, as a pharmaceutical composition also comprising a pharmaceutically acceptable carrier. The formulation of the Polymorph and dosages thereof are generally as disclosed for Compound (I) in International Patent Application, Publication Number WO94/05659 or WO98/55122.

Accordingly, the present invention also provides a pharmaceutical composition comprising the Polymorph and a pharmaceutically acceptable carrier therefor.

The Polymorph is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles. reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

In addition such compositions may contain further active agents such as anti-hypertensive agents and diuretics.

In addition, the Polymorph may be used in combination with other antidiabetic agents such as insulin secretagogues, for example sulphonylureas, biguanides, such as metformin, alpha glucosidase inhibitors, such as acarbose, beta agonists, and insulin such as those disclosed in WO98/57649, WO98/57634, WO98/57635 or WO98/57636. The other antidiabetic agents, the amounts thereof and methods of administration are as described in the above mentioned publications. The formulation of the Polymorph and dosages thereof in said combinations are generally as disclosed for Compound (I) in the above mentioned publications.

As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of the Polymorph to a human or non-human mammal in need thereof.

Conveniently, the active ingredient may be administered as a pharmaceutical composition hereinbefore defined, and this forms a particular aspect of the present invention.

In the treatment and/or prophylaxis of diabetes mellitus, conditions associated with diabetes mellitus and certain complications thereof the Polymorph may be taken in doses, such as those described above.

Similar dosage regimens are suitable for the treatment and/or prophylaxis of non-human mammals.

In a further aspect the present invention provides the use of the Polymorph for the manufacture of a medicament for the treatment and/or prophylaxis of diabetes mellitus, conditions associated with diabetes mellitus and certain complications thereof.

No adverse toxicological effects are indicated in the above mentioned treatments for the compounds of the invention.

The following example illustrates the invention but do not limit it in any way.

EXAMPLE 1

Preparation of Polymorph

Compound (I) (8.0 g) was suspended in acetone (80 ml) under nitrogen and the resulting slurry was stirred at reflux for 17.5 h. The mixture was then cooled to ambient and stirred for 30 min. The product was isolated by filtration, washed with acetone and dried in vacuo at 50° C. to give 6.9 g (86%) of the Polymorph.

EXAMPLE 2

Conversion of Polymorph to Compound (I)

Polymorph (18.0 g) was added to acetone (450 ml) and the resultant mixture was heated at reflux under nitrogen for 30 min. The hot solution was filtered, and the filtered solution was concentrated by distillation at atmospheric pressure (270 ml of acetone was collected). The concentrated solution was then allowed to cool at about 1° C./min and at 50° C. the solution was seeded with Compound (I) (0.09 g). Cooling at about 1° C./min was continued. The resulting slurry was stirred for 1 h at ambient temperature, then the solid was isolated by filtration, washed with acetone and dried in vacuo at 50° C. to give 15.1 g (84%) of Compound (I).

EXAMPLE 3

Conversion of Polymorph to Compound (I)

A mixture of Polymorph (10.0 g) in denatured ethanol (90 ml) was heated under nitrogen to give a clear solution. The clear solution was stirred at 62° C. for 30 min then filtered hot to a vessel preheated to 55° C. The filter was washed with hot denatured ethanol (10 ml). The temperature of the filtrate was adjusted to 60° C. before cooling, with stirring, at about 1 deg/min. The cooling mixture was seeded at 52° C. with Compound (I) (0.4 g) and cooling at 1° C./min with stirring was continued. The resultant slurry was stirred at ambient temperature for 1 h and the solid was isolated by filtration, washed with denatured ethanol and dried in vacuo at 50° C. to give 8.4 g (84%) of Compound (I).

CHARACTERISING DATA: The following characterising data were generated for the polymorph:

A Infrared

The infrared absorption spectrum of a mineral oil dispersion of the Polymorph was obtained using a Nicolet 710 FT-IR spectrometer at 2 $cm^{-1}$ resolution. Data were digitised at 1 $cm^{-1}$ intervals. The spectrum obtained is shown in FIG. I. Peak positions are as follows 1763, 1702, 1643, 1623, 1578, 1542, 1515, 1416, 1356, 1334, 1302, 1284, 1261, 1243, 1224, 1201, 1184, 1179, 1147, 1109, 1081, 1055, 1033, 1015, 975, 959, 912, 888, 856, 833, 798, 776, 759, 744, 722, 709, 651, 617, 604, 596, 581, 539, 524 and 505 $cm^{-1}$.

B Raman

The Raman spectrum of the Polymorph was recorded through a glass vial using a Perkin Elmer 2000R spectrometer at 4 $cm^{-1}$ resolution and is shown in FIG. II (X-axis shows Intensity, Y-axis shows Raman shift $cm^{-1}$, 1800–200 $cm^{-1}$). Excitation was achieved using a Nd:YAG laser (1064 nm) with a power output of 400 mW. Peak positions are as follows: 1762, 1703, 1613, 1586, 1546, 1469, 1446, 1389, 1333, 1315, 1284, 1264, 1249, 1206, 1181, 1147, 1082, 1035, 1014, 991, 969, 922, 912, 888, 840, 830, 778, 743, 722, 708, 654, 636, 618, 604, 541, 499, 468, 434, 411, 334, 290 and 235 $cm^{-1}$.

C Solid-State NMR

The 90.56 MHz $^{13}C$ CP-MAS NMR spectrum for the Polymorph is shown in FIG. III. Chemical shifts are tabulated in Table I. Data were recorded at ambient temperature and 10 kHz spinning frequency on a Bruker AMX360 spectrometer, with 1.6 ms cross polarization, and a repetition time of 15 s. Chemical shifts were externally referenced to the carboxylate signal of a glycine test sample at 176.4 ppm relative to tetramethylsilane, and are regarded as accurate to within +/− 0.5 ppm.

TABLE I $^{13}C$ Chemical Shifts of the Polymorph.
Chemical Shift (ppm)

| | | | | |
|---|---|---|---|---|
| 38.5 | 111.0 | 130.9 | 146.5 | 171.0 |
| 50.3 | 113.6 | 131.8 | 152.7 | 178.7 |
| 56.9 | 119.8 | 134.7 | 157.5 | |
| 66.0 | 129.1 | 138.7 | 169.5 | |

D X-Ray Powder Diffraction (XRPD)

The XRPD pattern of the Polymorph is shown below in FIG. IV and a summary of the XRPD angles and calculated lattice spacings characteristic of the Polymorph is given in Table II.

Data were acquired on a Bruker D8 Advance X-ray diffractometer with theta/theta geometry configured with a Cu anode, primary and secondary Soller slits, a secondary monochromator, and scintillation detector. The following acquisition conditions were used:

| | |
|---|---|
| Tube anode: | Cu |
| Generator tension: | 40 kV |
| Generator current: | 40 mA |
| Start angle: | 2.0° 2θ |
| End angle: | 35.0° 2θ |
| Step size: | 0.02° 2θ |
| Time per step: | 2.5 s |

X-Ray Powder Diffraction Angles and Calculated Lattice Spacings Characteristic of the Polymorph.

| Diffraction Angle (°2θ) | Lattice Spacing (Angstroms) |
|---|---|
| 9.9 | 8.97 |
| 12.5 | 7.07 |
| 13.1 | 6.78 |
| 15.1 | 5.87 |
| 15.5 | 5.72 |
| 16.7 | 5.30 |
| 18.9 | 4.69 |
| 20.3 | 4.38 |
| 21.2 | 4.19 |
| 21.7 | 4.09 |
| 22.1 | 4.02 |
| 22.9 | 3.88 |
| 23.4 | 3.80 |
| 23.9 | 3.72 |
| 24.6 | 3.61 |
| 25.2 | 3.53 |
| 25.7 | 3.46 |
| 26.3 | 3.39 |
| 27.1 | 3.29 |
| 27.5 | 3.25 |
| 27.9 | 3.20 |
| 28.7 | 3.11 |
| 29.1 | 3.07 |
| 30.1 | 2.97 |
| 30.5 | 2.93 |
| 30.8 | 2.91 |
| 31.3 | 2.85 |
| 31.7 | 2.82 |
| 32.9 | 2.72 |

-continued

X-Ray Powder Diffraction Angles and Calculated Lattice Spacings Characteristic of the Polymorph.

| Diffraction Angle (°2θ) | Lattice Spacing (Angstroms) |
|---|---|
| 33.2 | 2.69 |
| 33.8 | 2.65 |
| 34.0 | 2.64 |

What is claimed is:

1. A compound which is a polymorphic form of 5-[4-[2-(N-methyl-N-(2-pyridyl)amino)ethoxy]benzyl]thiazolidine-2,4-dione, maleic acid salt, wherein said compound provides at least one of:

(i) an infra red spectrum containing peaks at 1763, 912, 856 and 709 $cm^{-1}$;
   (ii) a Raman spectrum containing peaks at 1762, 1284, 912 and 888 $cm^{-1}$;
   (iii) a solid-state $^{13}C$ nuclear magnetic resonance spectrum containing peaks at 111.0, 113.6, 119.8, 129.1, 130.9, 131.8, 134.7, 138.7, 146.5, 152.7, 157.5, 169.5. 171.0, 178.7 ppm; and
   (iv) an X-ray powder diffraction pattern having calculated lattice spacings at 5.87, 5.30, 4.69, 4.09, 3.88, 3.61, 3.53 and 3.46 Angstroms.

2. A compound which is a polymorphic form of 5-[4-[2-(N-methyl-N-(2-pyridyl)amino)ethoxy]benzyl]thiazolidine-2,4-dione, maleic acid salt, wherein said compound, in a mineral oil dispersion, provides an infrared spectrum substantially in accordance with FIG. I.

3. A compound which is a polymorphic form of 5-[4-[2-N-methyl-N-(2-pyridyl)amino)ethoxy]benzyl]thiazolidine-2,4-dione, maleic acid salt, wherein said compound provides a Raman spectrum substantially in accordance with FIG. II.

4. A compound which is a polymorphic form of 5-[4-[2-(N-methyl-N-(2-pyridyl)amino)ethoxy]benzyl]thiazolidine-2,4-dione, maleic acid salt, wherein said compound provides a solid-state $^{13}C$ nuclear magnetic resonance spectrum substantially in accordance with FIG. III.

5. A compound which is a polymorphic form of 5-[4-[2-(N-methyl-N-(2-pyridyl)amino)ethoxy]benzyl]thiazolidine-2,4-dione, maleic acid salt, wherein said compound provides a solid-state $^{13}C$ nuclear magnetic resonance spectrum substantially in accordance with Table I:

TABLE I

| Chemical Shift (ppm) | | | | |
|---|---|---|---|---|
| 38.5 | 111.0 | 130.9 | 146.5 | 171.0 |
| 50.3 | 113.6 | 131.8 | 152.7 | 178.7 |
| 56.9 | 119.8 | 134.7 | 157.5 | |
| 66.0 | 129.1 | 138.7 | 169.5. | |

6. A compound which is a polymorphic form of 5-[4-[2-(N-methyl-N-(2-pyridyl)amino)ethoxy]benzyl]thiazolidine-2,4-dione, maleic acid salt, wherein said compound provides an X-ray powder diffraction pattern substantially in accordance with FIG. IV.

7. A compound which is a polymorphic form of 5-[4-[2-(N-methyl-N-(2-pyridyl)amino)ethoxy]benzyl]thiazolidine-2,4-dione, maleic acid salt, wherein said compound provides an X-ray powder diffraction pattern substantially in accordance with Table II:

TABLE II

| Diffraction Angle (°2θ) | Lattice Spacing (Angstroms) |
|---|---|
| 9.9 | 8.97 |
| 12.5 | 7.07 |
| 13.1 | 6.78 |
| 15.1 | 5.87 |
| 15.5 | 5.72 |
| 16.7 | 5.30 |
| 18.9 | 4.69 |
| 20.3 | 4.38 |
| 21.2 | 4.19 |
| 21.7 | 4.09 |
| 22.1 | 4.02 |
| 22.9 | 3.88 |
| 23.4 | 3.80 |
| 23.9 | 3.72 |
| 24.6 | 3.61 |
| 25.2 | 3.53 |
| 25.7 | 3.46 |
| 26.3 | 3.39 |
| 27.1 | 3.29 |
| 27.5 | 3.25 |
| 27.9 | 3.20 |
| 28.7 | 3.11 |
| 29.1 | 3.07 |
| 30.1 | 2.97 |
| 30.5 | 2.93 |
| 30.8 | 2.91 |
| 31.3 | 2.85 |
| 31.7 | 2.82 |
| 32.9 | 2.72 |
| 33.2 | 2.69 |
| 33.8 | 2.65 |
| 34.0 | 2.64. |

8. A process for preparing the compound according to claim 1, comprising:

suspending 5-[4-[2-(N-methyl-N-2-pyridyl)amino)ethoxy]benzyl]thiazolidine-2,4-dione, maleic acid salt in acetone; stirring the suspension at an elevated temperature for an extended period of time; and recovering the compound.

9. A process for preparing the compound according to any one of claims 1–7, comprising:

seeding a solution of 5-[4-[2-(N-methyl-N-(2-pyridyl)amino)ethoxy]benzyl]thiazolidine-2,4-dione, maleic acid salt in denatured ethanol at an elevated temperature with crystals of the compound; cooling the seeded solution; and recovering the compound from the denatured ethanol.

10. A pharmaceutical composition comprising an effective, non-toxic amount of the compound according to any one of claims 1–7 and a pharmaceutically acceptable carrier therefor.

11. A method for the treatment of diabetes mellitus, conditions associated with diabetes mellitus and certain complications thereof, in a human or non-human mammal which comprises administering an effective, non-toxic, amount of the compound according to any one of claims 1–7 to a human or non-human mammal in need thereof.

12. A method for the treatment of Type II diabetes in a human comprising administering an effective, non-toxic amount of the compound according to any one of claims 1–7 to a human in need thereof.

13. A method of claim 12, wherein the administrating comprises oral administration.

14. A method of claim 13, wherein the compound is administered in the form of a tablet or capsule for said oral administration.

15. A composition according to claim 10 which is adapted for oral administration.

16. A composition according to claim 15 which is in the form of a tablet or a capsule for said oral administration.

17. A compound which is a polymorphic form of 5-[4-[2-(N-methyl-N-(2-pyridyl)amino)ethoxy]benzyl]thiazolidine-2,4-dione, maleic acid salt, wherein said compound provides:

(i) an infra red spectrum containing peaks at 1763, 912, 856 and 709 cm$^{-1}$;

(ii) a Raman spectrum containing peaks at 1762, 1284, 912 and 888 cm$^{-1}$;

(iii) a solid-state $^{13}$C nuclear magnetic resonance spectrum containing peaks at 111.0, 113.6, 119.8, 129.1, 130.9, 131.8, 134.7, 138.7, 146.5, 152.7, 157.5, 169.5, 171.0, 178.7 ppm; and (iv) an X-ray powder diffraction pattern having calculated lattice spacings at 5.87, 5.30, 4.69, 4.09, 3.88, 3.61, 3.53 and 3.46 Angstroms.

18. A pharmaceutical composition consisting essentially of an effective, non-toxic amount of the compound according to any one of claims 1–7 and a pharmaceutically acceptable carrier therefor.

19. A method for the preparation of a pharmaceutical composition comprising admixing an effective, non-toxic amount of the compound according to any one of claims 1–7 with a pharmaceutically acceptable carrier therefor.

* * * * *